United States Patent [19]

Kirby et al.

[11] 3,987,029

[45] Oct. 19, 1976

[54] ANTIBACTERIAL ANTIBIOTICS AM31α, AM31β AND AM31γ

[75] Inventors: Jane Parsons Kirby, New City; Donald Bruce Borders, Suffern, both of N.Y.

[73] Assignee: American Cyanamid Company, Stamford, Conn.

[22] Filed: Mar. 19, 1975

[21] Appl. No.: 559,998

Related U.S. Application Data

[63] Continuation-in-part of Ser. No. 436,008, Jan. 23, 1974, abandoned.

[52] U.S. Cl. ............................... 536/17; 195/31 R; 195/80 R; 260/584 R; 424/181; 536/4; 536/18

[51] Int. Cl.² .................. C07H 15/12; C07H 15/04
[58] Field of Search ................... 260/210 R, 210 AB

[56] References Cited
UNITED STATES PATENTS 3,723,617   3/1973   Sutton ........................... 260/210 R Primary Examiner—Johnnie R. Brown
Attorney, Agent, or Firm—Denis A. Polyn

[57] ABSTRACT

This disclosure describes a novel class of antibiotics, three of which have been designed AM31α, AM31β, and AM31γ and are produced in a microbiological fermentation under controlled conditions using a new strain of *Streptoverticillium netropsis*.

15 Claims, 2 Drawing Figures

FIG. 1 PROTON MAGNETIC RESONANCE SPECTRUM OF A MIXTURE OF AM31α, AM31β, AND AM31γ IN DEUTERATED DIMETHYLSULFOXIDE

ANTIBACTERIAL ANTIBIOTICS AM31α, AM31β AND AM31γ

CROSS REFERENCE TO RELATED APPLICATION

This application is a continuation-in-part of our co-pending application Ser. No. 436,008, filed Jan. 23, 1974, and now abandoned.

BRIEF SUMMARY OF THE INVENTION

This invention relates to new organic compounds and, more particularly, is concerned with novel antibiotics which may be represented by the following structural formula:

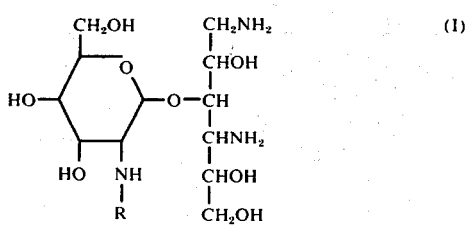

wherein R is hydrogen, formyl, or alkanoyl having up to 12 carbon atoms. The three antibiotics wherein R is hydrogen, acetyl, or propionyl in the above formula have been designated AM31α, AM31γ, and AM31β, respectively, and are produced by fermentation. Those compounds wherein R is formyl or alkanoyl in the above formula may be readily prepared by formylating or alkanoylating antibiotic AM31α by standard methods well known in the art. The present invention includes within its scope the antibiotics in dilute form, as crude concentrates, and in pure crystalline form. The structure of these new antibiotics as well as their spectral and chromatographic properties differentiate them from previously described antibacterial agents.

The novel antibiotics of the present invention form acid-addition salts with a variety of pharmaceutically acceptable organic and inorganic salt forming reagents. Thus, acid-addition salts, formed by admixture of the antibiotic base with one, two, or three (when R is hydrogen) equivalents of an acid, suitably in a neutral solvent, are formed with such acids as sulfuric, phosphoric, hydrochloric, hydrobromic, nitric, citric, lactic, tartaric, acetic, and related acids. For purposes of this invention, the antibiotic free bases are equivalent to their non-toxic acid-addition salts.

DETAILED DESCRIPTION OF THE INVENTION

Figure 1:
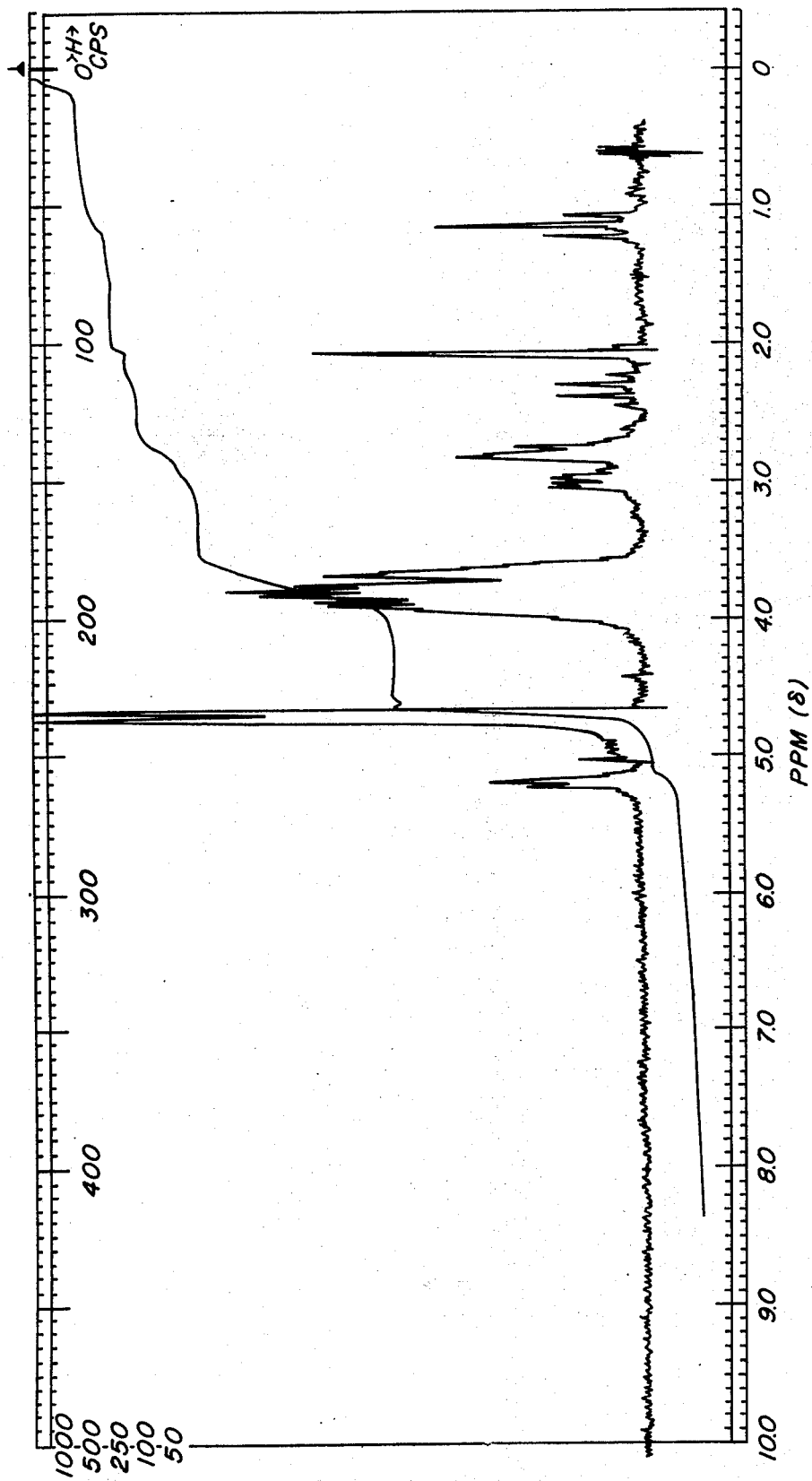

The new antibiotics designated AM31α, AM31β, and AM31γ are formed during the cultivation under controlled conditions of a new strain of *Streptoverticillium netropsis*. This new antibiotic producing strain was isolated from a soil sample collected near Emma, Indiana. A viable culture of the new microorganism has been deposited with the Culture Collection Laboratory, Northern Utilization Research and Development Division, United States Department of Agriculture, Peoria, Illinois, and has been added to its permanent collection. It is freely available to the public in this depository under its accession number NRRL 5774.

The description and identification of this new microorganism, maintained in the culture collection of the Lederle Laboratories Division, American Cyanamid Company, Pearl River, New York as Culture No. AM31, was supplied by Dr. H. D. Tresner of these laboratories. The following is a general description of the microorganism *Streptoverticillium netropsis*, based on diagnostic characteristics observed. Observations were made of the cultural, physiological and morphological features of the organism in accordance with the methods detailed by Shirling and Gottlieb (1). Descriptive details are recorded in Tables I–IV, and a general description of the culture is given below. Underscored descriptive colors were taken from Jacobson et al. (2).

[1] Shirling, E. B. and D. Gottlieb. 1966. Methods for characterization of Streptomyces species. Internat. Journ. Syst. Bacteriol. 16:313–340.
[2] Jacobson, E. et al. 1948. Color Harmony Manual. 3rd edit. Container Corporation of America, Chicago.

Amount of Growth

Heavy on Bennett's, Kuster's Oatflake, Hickey and Tresner's, Tomato Paste Oatmeal and Pablum agars; good on Yeast Extract, Asparagine Dextrose, Benedict's and Rice agars; moderate on Potato Dextrose and light on Czapek's Solution agars.

Aerial Mycelium and Sporulation

Aerial mycelium pinkish-white, becoming Pearl Pink (3 ca) to Bisque (4 ec) to Cork Tan (4 ie) in sporulating zones on most media.

Soluble Pigments

Yellowish to yellowish-brown or brownish on several media; none on Yeast Extract, Inorganic Salts-Starch and Czapek's Solution Agars.

Reverse Color

Yellowish brown to brownish on most media.

Miscellaneous Physiological Reactions

Complete peptonization of purple milk; no curd formation; no nitrate reduction in 14 days; gelatin completely liquefied in 7 days; only race of melanoid pigments formed on petone-iron agar; NaCl tolerance in yeast Extract agar ≧ 7% but <10%. Carbon source utilization, according to the Pridham and Gottlieb (3) method as follows: Good utilization of i-inositol, glycerol, d-trehalose, and dextrose; poor to no utilization of adonitol, l-arabinose, d-galactose, d-fructose, lactose, d-mannitol, d-meliboise, d-raffinose, l-rhamnose, salicin, sucrose, and d-xylose.

[3] Pridham, T. G. and D. Gottlieb. 1948. The utilization of carbon compounds by some Actinomycetales as an aid for species determination. J. Bacteriol. 56:107–114.

Micromorphology

Spore chains as regularly-spaced monoverticillate branches on aerial mycelium. Individual spore chains frequently terminating in hooks or coils of one or two turns. Spores elongate, cylindrical. Most spore chains contain some phalangiform spores. Spores 0.5–0.6 μM × 1.0–1.2 μM. Spore surfaces smooth as determined by transmission electron miscroscopy. Culture No. AM31 belongs to the genus Streptoverticillium of the Actinomycetales. This genus is characterized by having its spore chains borne in whorls or verticils; there are about 40 members recognized. When compared with published descriptions (4) (5) as well as with available reference specimens, Culture No. AM31 conforms most closely to the species concept for the taxon *Streptoverticillium netropsis*.

[4] Locci, R., E. Baldacci, and B. Petrolini Baldan. 1969. The genus Streptoverticillium. A toxonomic study. Giornale di Microbiologia 17:1–60.

(5)Shirling, E. S. and D. Gottlieb. 1968. Cooperative description of type cultures of Streptomyces III. Internat. Journ. Syst. Bacteriol. 18:279-392.

TABLE I

Cultural Characteristics of *Streptoverticillium netropsis* NRRL 5774

Incubation: 14 days
Temperature: 28° C.

| Medium | Amount of Growth | Aerial Mycelium and/or Spores | Soluble Pigment | Reverse Color | Remarks |
|---|---|---|---|---|---|
| Yeast Extract Agar | Good | Aerial mycelium pinkish-white becoming Bisque (4 ec) to Cork Tan (4 ie) in sporulating areas. Sporulation good. | None | Lt. Amber (3 ic) | |
| Asparagine Dextrose Agar | Good | Aerial mycelium pinkish-white becoming Bisque (4 ec) to Cork Tan (4 ie) in sporulating areas. Sporulation good. | Yellowish-brown; light | Cocoa Brown (5 ni) | |
| Benedict's Agar | Good | Aerial mycelium pinkish-white becoming Bisque (4 ec) in sporulating areas. Sporulation moderate. | Yellowish; light | Lt. Amber (3 ic) | Abundant colorless exudate on colonies. |
| Bennett's Agar | Heavy | Aerial mycelium pinkish-white becoming Bisque (4 ec) to Cork Tan (4 ie) in sporulating areas. Sporulation heavy. | Yellowish-brown; light | Cocoa Brown (5 ni) | Abundant yellowish exudate on colonies. |
| Inorganic Salts Starch Agar | Good | Aerial mycelium pinkish-white becoming Bisque (4 ec) to Cork Tan (4 ie) in sporulating areas. Sporulation good. | None | Cork Tan (4 ie) | |
| Kuster's Oatflake Agar | Heavy | Aerial mycelium pinkish-white becoming Bisque (4 ec) to Cork Tan (4 ie) in sporulating areas. Sporulation heavy. | Brownish; moderate | Lt. Spice Brown (4 lg) | |
| Czapek's Solution Agar | Light | Aerial mycelium pinkish-white becoming Bisque (4 ec) in sporulating areas. Sporulation light. | None | Pearl Pink (3 ca) | |
| Potato Dextrose Agar | Moderate | Aerial mycelium pinkish-white becoming Pearl Pink (3 ca) to Bisque (4 ec) in sporulating areas. Sporulation light. | Yellowish-brown; moderate | Lt. Brown (4 ng) | Abundant colorless exudate on colonies |
| Hickey & Tresner's Agar | Heavy | Aerial mycelium pinkish-white becoming Bisque (4 ec) to Cork Tan (4 ie) in sporulating areas. Sporulation heavy. | Brown; heavy | Dk. Wine (7 pi) | |
| Tomato Paste Oatmeal Agar | Heavy | Aerial mycelium pinkish-white becoming Bisque (4 ec) to Cork Tan (4 ie) in sporulating areas. Sporulation heavy. | Brown; heavy | Cocoa Brown (5 ni) | Abundant yellowish brownish-trudate on colonies. |
| Pablum Agar | Heavy | Aerial mycelium pinkish-white becoming bisque (4 ec) in sporulating areas. Sporulation heavy. | Brownish; light | Lt. Spice Brown (4 lg) light | |
| Rice Agar | Good | Aerial mycelium pinkish-white becoming Pearl Pink (3 ca) to Bisque (4 ec) in sporulating areas. Sporulation moderate. | Yellowish-brown; light | Lt. Brown (4 ng) | |

TABLE II

Micromorphology of *Streptoverticillium netropsis* NRRL 5774

| Medium | Aerial Mycelium and/or Sporiferous Structures | Spore Shape | Spore Size | Spore Surface |
|---|---|---|---|---|
| Inorganic Salts-Starch Agar | Spore chains as regularly-spaced monoverticillate branches on aerial mycelium. Individual spore chains frequently terminating in hooks or Coils of one or two turns. | Spores elongate, cylindrical. Most spore chains contain some phalangiform spores. | 0.5–0.6 μM × 1.0–1.2 μM | Spore surfaces smooth as determined by transmission electron microscopy. |

TABLE III

Miscellaneous Physiological Reaction of *Streptoverticillium netropsis* NRRL 5774

Temperature: 28° C.

| Medium | Incubation Period | Amount of Growth | Physiological Reaction |
|---|---|---|---|
| Purple Milk | 14 days | Good | Complete peptonization; no curd remaining |
| Organic Nitrate Broth | 7 days | Good | No nitrate reduction |
| Organic Nitrate Broth | 14 days | Good | No nitrate reduction |
| Gelatin | 7 days | Good | Gelatin completely liquified |
| Peptone-iron Agar | 48 hours | Good | Trace of melanoid pigments |
| Yeast Extract Agar plus (4, 7, 10 and | | | |

TABLE III-continued

Miscellaneous Physiological Reaction of *Streptoverticillium netropsis* NRRL 5774

Temperature: 28° C.

| Medium | Incubation Period | Amount of Growth | Physiological Reaction |
|---|---|---|---|
| 13%) NaCl | 10 days | Good | NaCl tolerance ≧ 7% but <10% |

TABLE IV

Carbon Source Utilization Pattern of *Streptoverticillium netropsis* NRRL 5774

Incubation: 10 days
Temperature: 28° C.

| Carbon Source | Utilization* |
|---|---|
| Adonital | 0 |
| l-Arabinose | 0 |
| d-Galactose | 0 |
| d-Fructose | 0 |
| i-Inositol | 3 |
| Lactose | 0 |
| d-Mannitol | 0 |
| Glycerol | 3 |
| d-Melibiose | 0 |
| d-Raffinose | 0 |
| l-Rhamnose | 0 |
| Salicin | 1 |
| Sucrose | 0 |
| d-Trehalose | 3 |
| d-Xylose | 0 |
| Dextrose | 3 |
| Negative Control | 0 |

*3-Good Utilization
*2-Fair Utilization
*1-Poor Utilization
*0-No Utilization

It is to be understood that for the production of the new antibiotics AM31α, AM31β, and AM31γ, the present invention is not limited to this particular microorganism or to microorganisms fully answering these growth and microscopic characteristics, which are given for illustrative purposes only. In fact, it is desired and intended to include the use of mutants produced from the described microorganism by various means such as exposure to X-radiation, ultraviolet radiation, nitrogen mustard, actinophages, and the like.

Fermentation Process

Cultivation of the microorganism *Streptoverticillium netropsis* NRRL 5774 may be carried out in a wide variety of liquid culture media. Media which are useful for the production of these three antibiotics include an assimilable source of carbon such as starch, sugar, molasses, glycerol, etc., an assimilable source of nitrogen such as protein, protein hydrolysate, polypeptides, amino acids, corn steep liquor, etc., and inorganic anions and cations, such as sodium, potassium, calcium, sulfate, phosphate, chloride, etc. Trace elements such as boron, polybdenum, copper, etc., are supplied as impurities of other constituents of the medium. Aeration in tanks and bottles is provided by forcing sterile air through or onto the surface of the fermenting medium. Further agitation in tanks is provided by a mechanical impeller. An antifoaming agent, such as lard oil, may be added as needed.

Inoculum Preparation

Shaker flask inoculum of *Streptoverticillium netropsis* NRRL 5774 is prepared by inoculating 100 ml. of sterile liquid medium in 500 ml. flasks with scrapings or washings of spores from an agar slant of the culture. The following is an example of a suitable medium:

| | |
|---|---|
| corn starch | 24 gm. |
| bacto tryptone | 5 gm. |
| Yeast extract | 5 gm. |
| Beef extract | 3 gm. |
| Glucose | 1 gm. |
| Water to | 1000 ml. |

The pH is adjusted to 7.0 with NaOH.

The flasks are incubated at a temperature from 25°–29°C., preferably 28°C., and agitated vigorously on a rotary shaker for 30 to 48 hours. These 100 ml. portions of inoculum are used to inoculate one and twelve liter batches of the same medium in 2 liter and 20 liter glass fermentors at 28°C. The inoculated mash is aerated with sterile air while growth is continued for 40 to 55 hours. These batches are used to inoculate tank fermentors.

Tank Fermentation

For the production of antibiotics AM31α, AM31β, and AM31γ in tank fermentors the following medium is preferably used:

| | |
|---|---|
| Soy flour | 40 gm. |
| Molasses | 20 gm. |
| Glucose | 10 gm. |
| Calcium carbonate | 3 gm. |
| Water to | 1000 ml. |

Each tank is inoculated with 3 to 10% of inoculum made as described above. Aeration is supplied at the rate of 0.2 to 0.8 liter of sterile air per liter of broth per minute and the fermenting mixture is agitated by an impeller driven at 200 to 400 rpm. The temperature is maintained at 25°–29°C., usually at 28°C. The fermentaion is ordinarily continued for 80 to 100 hours, at which time the mash is harvested.

Isolation of AM31α, AM31β, and AM31γ as a Mixture

After the fermentation is completed, the harvested mash is filtered and the filtrate, at pH 7.8, is passed through a 5 liter Amberlite IRC-50 (a methacrylic acid-divinyl benzene ion exchange resin) ($NH_4+$) column at a flow rate of 250 ml./minute. After the column is washed with 25 liters of deionized water, the antibiotic activity is eluted with 30 liters of 2N $NH_4OH$ and detected by the conventional disc agar diffusion assay against *Klebsiella pneumoniae*. The 30 liters of eluate at pH 11.7 is reduced to 2 liters and adjusted to pH 8.1 with 0.1N HCl. The antibiotics in this concentrate are adsorbed onto an Amberlite CG-50 (a methacrylic acid-divinyl benzene ion exchange resin) ($NH_4+$) column and eluted with 1.5N $NH_4OH$. The column eluate is concentrated to 65 ml. of an orange viscous syrup on a rotary evaporator. This concentrate is passed through a Dowex 1-X2 (a trimethylbenzylammonium polystyrene cross linked with 2% divinyl benzene) (OH⁻) (50–100 mesh) column and the column is developed with water. The bioactive effluent is divided into 2 major fractions based on visible color and bioactivity. One fraction (I) contans a mixture of AM31α, β, and as a white powder that is essentially free of unwanted impurities. The fraction, obtained in a liquid state because of impurities, may be further processed to yield more antibiotic mixture. This liquid fraction is passed through a Dowex 1-X2 (OH⁻) (200–400 mesh) column. The column is developed with water and 3 major fractions are obtained, two (II and IV) as a white powder and one (III) as a thick yellow syrup. This yellow syrup is further purified by adsorption on a Dowex ® 50X9 (a sulfonated polystyrene cross linked with 8% divinyl benzene) (H+) column. The column is rinsed with 250 ml. of water and the antibiotics are eluted with 500 ml. of 1.5N NH₄OH. Two bioactive fractions are obtained in the 60–70 ml. and 290–700 ml. portions of column eluate. Each fraction is reduced to a small volume on a rotary evaporator and then freeze-dried yielding a fine white powder (V) and a white hygroscopic powder (VI). All of the fractions contain mixtures of the three components.

Separation of AM31α, AM31β, and AM31γ by Paper Chromatography

Components are differentiated from each other by paper chromatography using l-butanol saturated with water to which 2% p-toluenesulfonic acid is added. The $R_f$ values are: 0.61; 0.43; and 0.31, obtained by minhydrin.

In vitro Activity

The mixture of antibiotics AM31α, β, and γ are active against a wide variety of gram positive and gram negative bacteria as determined by the standard agar-well diffusion technique. The results of such a test on the complex of the three components appear in Table V.

TABLE V

| Name of Organism | Inhibition Zone (mm)* |
|---|---|
| Bacillus cereus (Waksman) | 2.9 |
| Klebsiella pneumoniae (Friedlanders) | 5.8 |
| Alcaligenes sp. ATCC 10153 | 4.1 |
| Bacillus subtilis (Stansly R-78) | 5.8 |
| Bacillus subtilis (Resistant | 1.0 |

TABLE V-continued

| Name of Organism | Inhibition Zone (mm)* |
|---|---|
| to Streptothricin) (Stansly R-76) | |
| Mycobacterium smegmatis (No. 607) | 2.6 |
| Staphylococcus aureus (resistant to tetracycline) | 2.5 |
| Escherichia coli (Parke Davis) | 4.0 |
| Escherichia coli (resistant to chloramphenicol) | 7.3 |
| Staphylococcus aureus 209P (resistant to erythromycin) | 6.5 |
| Corynebacterium xerosis NRRL B-1397 | 8.5 |
| Salmonella gallinarum No. 605 | 7.3 |
| Staphylococcus aureus (Smith) | 5.3 |
| Klebsiella pneumoniae (AD) | 9.2 |
| Pseudomonas aeruginosa ATCC 10145 | 4.6 |
| Escherichia coli (Upjohn) Culture) | 4.8 |
| Aerobacter aerogenes | 5.2 |
| Proteus mirabilis | 1.6 |
| Salmonella typhosa ATCC 6539 | 7.4 |
| Staphylococcus aureus ATCC 14154 | 1.3 |
| Escherichia coli 311 | 5.0 |
| Pseudomonas aeruginosa PA7 | 3.6 |

*Zone value given as distance from edge of well to outer edge of inhibition zone.

In vivo Results

The three antibacterial components AM31α, AM31β, and AM31γ are active in vivo against a variety of organisms. These new antibacterials are thereby potentially useful as therapeutic agents in treating bacterial infections in mammals. These new antibacterials can be expected to be usefully employed for treating or controlling bacterial infections by parenteral administration. The usefulness of these new antibacterial agents is demonstrated by their ability to control systemic lethal infections in mice. A mixture of these three new antibiotics shows high in vivo antibacterial activity in mice against Escherichia coli, Salmonella typhosa and Klebsiella pneumoniae when administered by a single subcutaneous dose to groups of Carworth Farms CF-1 mice, weighing about 20 gm., infected intraperitoneally with 0.5 ml. of the indicated broth dilution of 5 hour cultures of the following organisms: Escherichia coli, $10^{-3}$; Salmonella typhosa undiluted; Klebsiella pneumoniae, $10^{-4}$. Table VI below, illustrates the in vivo antibacterial activity of a mixture of AM31α, AM31β, and AM31γ against these three bacteria.

TABLE VI

| | Alive/Total Mice Treated 7 Days After Infection |
|---|---|
| Single Subcutaneous Dose mg./kg. | Escherichia coli |
| 512 | 2/2 |
| 256 | 2/2 |
| 128 | 2/2 |
| 64 | 2/2 |
| 32 | 0/2 |
| Infected non-treated controls | 2/10 |
| Single Subcutaneous Dose Mg./kg. | Salmonella typhosa |
| 512 | 2/2 |
| 256 | 2/2 |
| 128 | 2/2 |
| 64 | 0/2 |
| Infected non-treated controls | 0/10 |
| Single Subcutaneous Dose mg./kg. | Klebsiella pneumoniae |
| 512 | 2/2 |
| 256 | 2/2 |
| 128 | 0/2 |
| 64 | 0/2 |

TABLE VI-continued

| | Alive/Total Mice Treated 7 Days After Infection |
|---|---|
| Infected non-treated controls | 0/10 |

This invention will be described in greater detail in conjunction with the following specific examples.

EXAMPLE 1

Inoculum Preparation

A typical sterile medium used to grow the primary inoculum was prepared according to the following formula:

| | |
|---|---|
| Corn starch | 24 gm. |
| Bacto tryptone | 5 gm. |
| Yeast extract | 5 gm. |
| Beef extract | 3 gm. |
| Glucose | 1 gm. |
| Water to | 1000 ml. |

The pH was adjusted to 7.0 with NaOH

Washer of scraped spores from an agar slant of *Streptoverticillium netropsis* NRRL 5774 were used to inoculate two 500 ml. flasks containing 100 ml. each of the above sterile medium. The flasks were placed on a rotary shaker and agitated vigorously for 48 hours at 28°C. The resulting flask inoculum was transferred to a 5 gallon glass fermentor containing 12 liters of the same sterile medium. The inoculum mash was aerated with sterile air while growth was carried out for 48 hours at 28°C., after which the contents were used to seed a 300 liter tank fermentor.

EXAMPLE 2

Fermentation

A fermentation medium was prepared according to the following formula:

| | |
|---|---|
| Soy flour | 40 gm. |
| Molasses | 20 gm. |
| Glucose | 10 gm. |
| Calcium carbonate | 3 gm. |
| Water to | 1000 ml. |

Twelve liters of inoculum, prepared as described in Example 1, were used to inoculate 300 liters of the above sterilized fermentation medium. The fermentation was carried out for 89 hours at 28°C. with an aeration rate of 0.5 liter of air/liter of mash/minute. The mash was agitated by an impeller driven at 300 rpm. The mash was harvested.

EXAMPLE 3

Isolation of a Mixture of AM31α, AM31β, and AM31γ

A 300 liter portion of whole harvest mash, prepared as described in Example 2, was filtered. The filtrate, having a pH of 7.8, was passed through a 5 liter Amberlite IRC-50 ($NH_4$+) column, 4 inch × 60 inch, at a flow rate of 250 milliters per minute. The column was washed with 25 liters of deionized water. The antibiotic activity was eluted with 30 liters of 2N $NH_4OH$ and detected by the disc agar diffusion assay against *Klebsiella pneumoniae*. The 30 liter eluate at pH 11.7 was reduced to 2 liters and adjusted to pH 8.1 with 0.1N HCl. One liter of this concentrate was adsorbed on an Amberlite CG-50 ($NH_4$+) 3 33 52 cm. column and eluted with 500 ml. of 1.5N $NH_4OH$. A duplicate run was made with the remaining one liter concentrate and the eluates from the two runs were combined and concentrated on a rotary evaporator to 65 ml. of an orange viscous syrup. This 65 ml. concentrate was passed through a Dowex 1-X2 ($OH^-$) (50-100 mesh) 2 × 54 cm. column and the column was developed with water. The bioactive effluent was divided into two fractions based on visible color and bioactivity. One fraction was recovered from 735–1200 ml. of column effluent. It was freeze dried to give 132 mg. of a white powder (I). The other fraction was from 270–734 ml. of column effluent. When this was freeze dried it remained in a liquid state, due to impurities. The liquid fraction was dissolved in water and the solution was passed through a Dowex 1X2 ($OH^-$) (200–400 mesh) 1.5 × 21 cm. column. As the column was developed with water, 3 major fractions were obtained with the indicated elution volumes: Fraction II, 55–114 ml.; Fraction IV, 361–775 ml.; and Fraction III, 115–360 ml. of column effluent. Fractions II and IV were freeze-dried to give 4.76 gm. and 215 mg. of white powder, respectively. Fraction III was concentrated to 75 ml. of yellow syrup which was adsorbed on a Dowex 50-X8 ($H^+$) 3 × 30 cm. column. This column was rinsed with 250 ml. of water and then eluted with 500 ml. of 1.5N $NH_4OH$. Two bioactive fractions were obtained in the 60–70 ml. and 290–700 ml. portions of the column effluent. Each fraction was reduced to a small volume on a rotary evaporator, freeze-dried and the solids were recovered, yielding 685 mg. of fine white powder (Fraction V) and 6.78 gm. of white hygroscopic powder (Fraction VI). Total yield, 12.572 gm.

Infrared and nuclear magnetic resonance spectra suggested that the above fractions were all mixtures with approximately the same composition of α, β and γ components.

Figure 2:
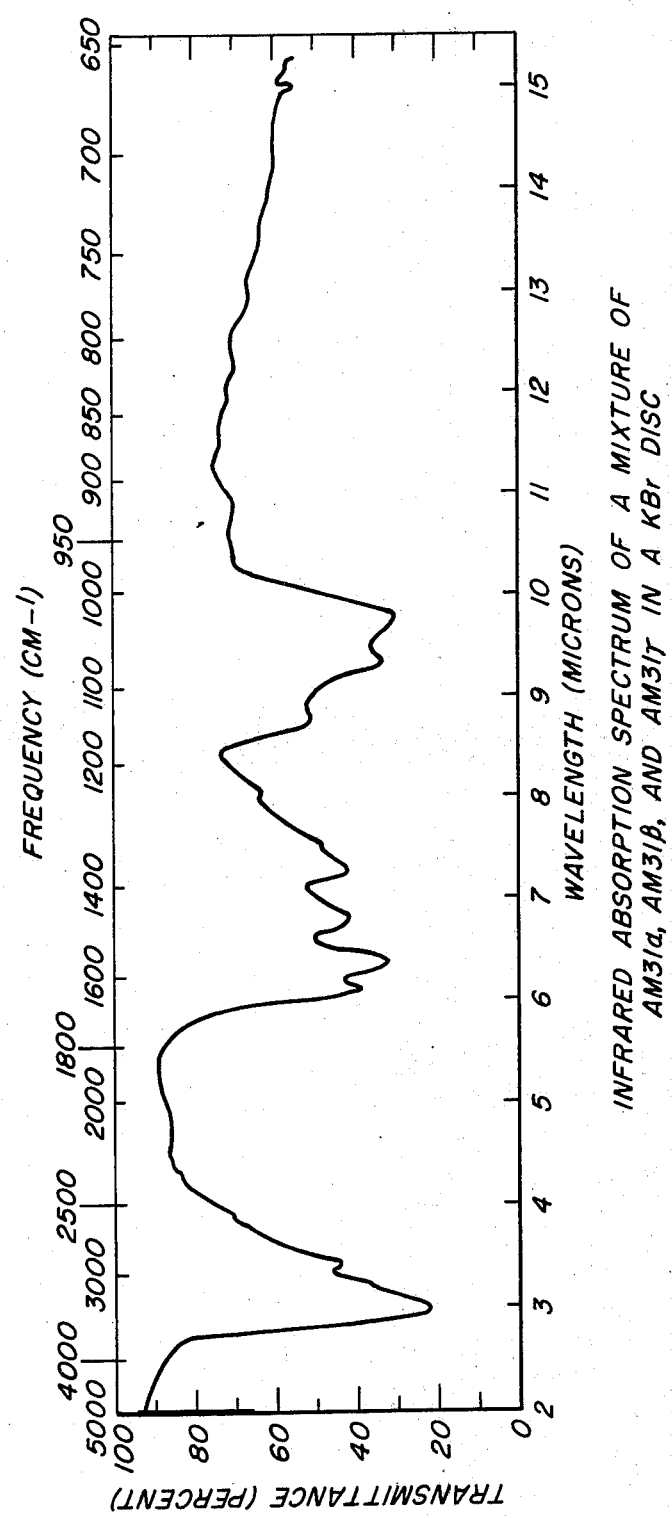

Fraction II had $[\alpha]_D^{25°} = + 85.0° \pm 2.4°$ (C 0.41, $H_2O$). Anal. Found: C, 42.03%; H, 8.08%; N, 10.47%. Nuclear magnetic resonance and infrared spectra of a mixture of components are given in FIGS. 1 and 2, respectively, of the accompanying drawings.

EXAMPLE 4

Preparation of N-acetyl-O-trimethylsilyl Derivative of Antibiotic AM31 Complex The N-acetyl-O-trimethylsilyl derivative of the antibiotic AM31 complex was prepared in the following way for mass spectrum characterization. Four milligrams of AM31 complex was mixed with 0.50 ml. of methanol and 0.30 ml. of acetic anhydride. The solution was allowed to remain overnight at room temperature. The N-acetylated derivative was precipitated with 3–4 ml. of diethyl ether, washed several times with diethyl ether and dried in a desiccator. The O-trimethylsilyl derivative was then made by adding 0.5 ml. of TRI-SIL (a ready mix formula containing trimethylchlorosilane from Pierce Chemical Company, Rockford, Ill.). The silylation proceeded in a desiccator for 2 hours at room temperature after which the excess reagent was removed under vacuum. The residue was redistributed in benzene. The benzene-soluble material was separated from any residual solids and the solution was evaporated to a residue in a stream of nitrogen. The data for the mass spectrum of the N-acetyl-O-trimethylsilyl derivative are given in Tables VII and IX. The mass spectrum of the degradation product of AM31 complex, N-acetyl-O-trimethylsilyl derivative of the diaminodideoxyalditol is given in Table VIII.

TABLE VII

High Resolution Mass Spectral Data for N-Acetyl-O-Trmethylsilyl Derivative of AM31 Complex

| Observed | Exact Mass Calculated | Composition |
| --- | --- | --- |
| 898.4324 | 898.4408 | $C_{36}H_{80}N_3O_{11}Si_6$ |
| 884.4238 | 884.4252 | $C_{35}H_{78}N_3O_{11}Si_6$ |
| 694.3380 | 694.3406 | $C_{28}H_{60}N_3O_8Si_4$ |
| 635.2995 | 635.3035 | $C_{26}H_{55}N_2O_8Si_4$ |
| 581.2909 | 581.2929 | $C_{23}H_{53}N_2O_7Si_4$ |
| 420.2056 | 420.2057 | $C_{17}H_{38}N_1O_5Si_3$ |

TABLE VIII

High Resolution Measurements of N-Acetyl-O-Trimethylsilyl Derivative of Diaminodideoxyalditol (the degradation product of AM31 Complex)

| Observed | Exact Mass Calculated | Composition |
| --- | --- | --- |
| 537.2668 | 537.2659 | $C_{21}H_{49}N_2O_6Si_4$ |
| 378.1952 | 378.1942 | $C_{15}H_{36}N_1O_4Si_3$ |
| 347.1822 | 347.1818 | $C_{14}H_{31}N_2O_4Si_2$ |
| 288.1450 | 288.1450 | $C_{12}H_{26}N_1O_3Si_2$ |
| 276.1421 | 276.1450 | $C_{11}H_{26}N_1O_3Si_2$ |
| 217.1081 | 217.1080 | $C_9H_{21}O_2Si_2$ |
| 198.0949 | 198.0959 | $C_9H_{16}N_1O_2Si$ |
| 186.0934 | 186.0950 | $C_8H_{16}N_1O_2Si$ |
| 174.0929 | 174.0950 | $C_7H_{16}N_1O_2Si$ |

TABLE IX

Relative Abundance of Selected Ions Observed in Gas Chromatography/Mass Spectum Analysis of N-Acetyl-O-Trimethylsilyl Derivative of AM31 Complex

| α and γ Components | | β Component | |
| --- | --- | --- | --- |
| Ion (m/e) | Relative Abundance % | Ion (m/e) | Relative Abundance % |
| 174 | 25 | 174 | 20 |
| 186 | 50 | 186 | 35 |
| 276 | 3.5 | 276 | 3.5 |
| 420 | 100 | 434 | 100 |
| 581 | 2.5 | 581 | 2.5 |
| 635 | 32.5 | 649 | 22.5 |
| 694 | 8.5 | 708 | 7.5 |
| 884 | 6.0 | 898 | 4.0 |

These spectra were obtained with a Varian CH7 Gas Chromatography/Mass Spectrum with resolution. M/ΔM 2000, ionizing voltage 70ev, and source temperature 200°C. Gas chromatography conditions were as follows: The column for the gas chromatography was 6 feet long. The support was 0.7% OV-1 on glass Chrom Q (mesh size 100–200). The column temperature was 230°C., injection port temperature 250°C., and detector temperature 210°C. The carrier gas was nitrogen. The retention times of the components were 24 minutes and 27.4 minutes.

EXAMPLE 5

Paper Chromatographic Separation of Antibiotic Components

The three components of the antibiotic mixture were differentiated using 1-butanol saturated with water to which 2% p-toluenesulfonic acid was added. The $R_f$ values for the components are 0.61, 0.43, and 0.31 as obtained by ninhydrin

EXAMPLE 6

Preparation and Identification of Diaminoalditol Fragment of Antibiotic AM31 Complex A 100 mg. sample of Antibiotic AM31 was heated in 5 ml. of 6N HCl for 16 hours at 140°C. The resulting hydrolysate was filtered to remove considerable black precipitate, evaporated to a residue and dissolved in one ml. of water. This solution was poured onto a 1 × 2 cm. Dowex 1-X2 (OH⁻) column (200–400 mesh), followed by 5 bed volumes of water. A dark brown hygroscopic solid (33.9 mg.) was recovered on freeze-drying the column effluent. A 10 mg. portion was used to prepare an N-acetyl-O-trimethylsilyl derivative for mass spectral studies as follows: Ten mg. of the product was mixed with 1.25 ml. of methanol and 0.75 ml. of acetic anhydride and allowed to remain overnight at room temperature. The N-acetylated compound was precipitated with 3–4 ml. of diethyl ether, washed several times with diethyl ether, dried in a desiccator and silylated with Tri-Sil (a ready mix formula of trimethyl chlorosilane from Pierce Chemical Company, Rockford, Ill.). The silylation proceeded in a desiccator for 2 hours at room temperature after which the reagent was removed under vacuum and the residue was redistributed in benzene. The benzene-soluble material was separated from any residual solids and the solution was evaporated to a clear resin in a stream of nitrogen.

EXAMPLE 7

Preparation and Identification of Glucosamine Fragment of Antibiotic AM31

A 5 mg. portion of antibiotic AM31 was dissolved in 3 ml. of 3N HCl and heated in a sealed vial at 100°–110°C. for 5 hours. The product was evaporated to a residue which was redissolved in water and evaporated to remove HCl fumes. The residue was dissolved in 0.5 ml. of water and spotted onto sheets of Whatman No. 1 paper. The papergrams were developed by the descending technique and the solvent allowed to drip off the sheets. The AM31 hydrolysate had a component not differentiated from glucosamine by mobility and color reactions in the following systems: 1-butanol:-puridine:water (6:4:3), 11.0 cm. distance from origin; ethyl acetate:puridine:water (72:20:23), 1.5 cm. distance from origin. Zones were detected by ninhydrin and the Tollens reagent.

EXAMPLE 8

Preparation of Butyryl Derivative of AM31α

A solution of 10 g. of a mixture of AM31β and AM31γ, 11.3 g. of dimedone, and 200 ml. of pyridine was refluxed for 7.5 hours, then allowed to stand at room temperature overnight. The pyridine was evaporated at reduced pressure and the residue was treated with 150 ml. of 1:1 methanol:water and 1.3 g. of dimedone and the resulting solution was refluxed for 6 hours. The solvent was removed completely at reduced pressure to yield a yellow gummy solid. Trituration with two 50 ml. portions of diethyl ether yielded, after air drying, 21.6 g. of yellow solid.

The solid was dissolved in 250 ml. of 1:1 methanol:-water and put on a column containing 350 ml. of Dowex 1-X2 (OH⁻) resin. The column was eluted with 1:1 methanol:water until no further product could be seen on a tlc plate (2.5 liters of eluent was used).

The eluate was put on a column containing 800 ml. of Dowex 50-X4 (H+) resin. The column was rinsed with 600 ml. of water, then eluted with 2% pyridine in water. The fraction of eluate between 2.5 and 5.5 liters contained the product. The solvent was removed at reduced pressure to yield a pale yellow gummy froth. This is the bis-dimedone derivative (II).

with about 100 ml. of water and the filtrate was put on a column of 700 ml. of Dowex 50-X4 (H⁺). The column was washed with one liter of water, 2 liters of 2% pyridine in water, and then eluted with 3 liters of 2N ammonium hydroxide. The eluate was evaporated at reduced pressure to yield a yellow froth (9.8 g.). The froth was lyophilized to yield 8.9 g. of very low density cream colored solid, the protected intermediate (III).

A solution of 11.8 g. of the protected intermediate (III) in 400 ml. of methanol was cooled to 5°C. and treated with 20 ml. of butyric anhydride. The mixture was stirred at 0°C. for one hour, then at room temperature for 16 hours. The solution was concentrated at reduced pressure, the residue was dissolved in 300 ml. of 1:1 methanol:water and put on a 700 ml. column of Dowex 50-X4 (H⁺). The column was washed with 2

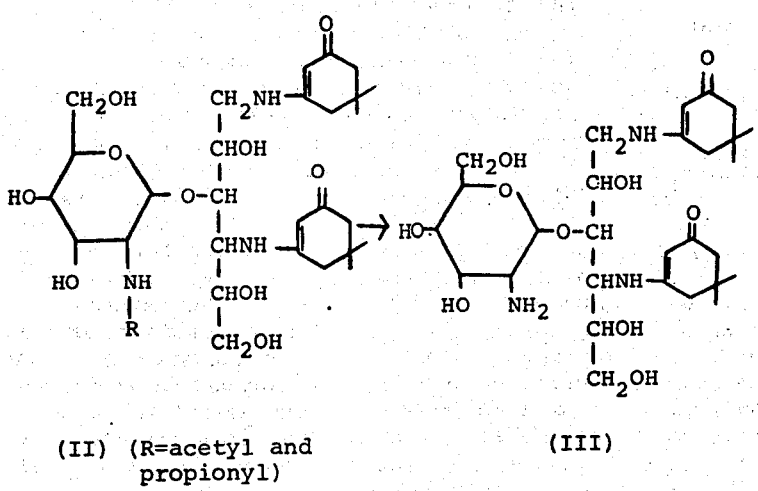

(II) (R=acetyl and propionyl)    (III)

The froth was dissolved in 200 ml. of water, treated with 25 g. of barium hydroxide hydrate and the mixture was refluxed 1.25 hours. The mixture was filtered and the filtrate was treated with carbon dioxide to pH 6.0. The mixture was filtered, the filter cake was washed liters of 1:1 methanol:water, then eluted with 2% pyridine in water. The product (IV) is eluted in the fraction between 2.5 and 4.5 liters of eluate. The eluate is evaporated at reduced pressure and the residual gum is hydrolyzed without further purification.

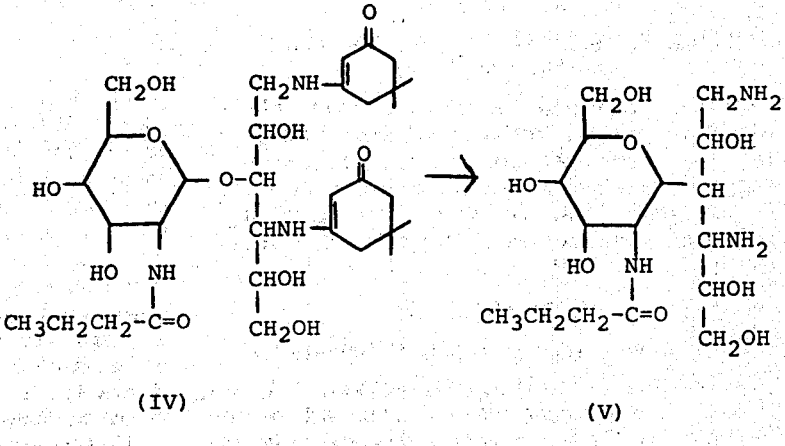

(IV)    (V)

The protected antibiotic (IV) (about 12 g.) was dissolved in 400 ml. of water, cooled to 0°–5°C., and treated with a prechilled (to 5°C.) solution of 3% chlorine in carbon tetrachloride. The mixture was treated with 50 ml. of methanol and stirred at 0°–5°C. for 0.5 hour. The layers were separated and the aqueous portion was washed with carbon tetrachloride (100 ml.), then with chloroform (2×100 ml.), and treated with concentrated ammonium hydroxide to pH 5.0 (required about 5 ml.). This solution was treated with a solution of sodium bisulfite in water to remove traces of chlorine (until no starch iodide test was obtained). Then retreated with ammonium hydroxide to pH 5.0 (required 4 ml. more). The solution of the crude antibiotic (V) was evaporated at reduced pressure to 25–50 ml. volume and submitted for chromatography.

EXAMPLE 9

Purification of Butyryl Derivative (V) of AM31

The solution (10 ml.) of the crude antibiotic (V) was placed onto a column (.15×22 cm.) of Amberlite XAD-2. The column was then eluted with 250 ml. of each of the following solvents: methanol, 50% aqueous methanol, and water. The antibiotic eluted from the column in 12–144 ml. of effluent and was detected by a paper disc agar-diffusion assay with *Kiebsiella pneumonia* as a test organism. This fraction was evaporated in vacuo to a residue which was dissolved in water and freeze dried to obtain 8.6 g. of white powder. Seven grams of this material was dissolved in a small volume of water and adsorbed onto a column (2×32 cm.) of Dowex 50-X8 (NH4+) 50–100 mesh. The column was rinsed with 250 ml. of water and then eluted with 250 ml. of 1.5N NH₄OH as 7 ml. fractions were collected. The antibiotic, detected in reactions 32–67 by the agar disc assay, was recovered by evaporating the pooled fractions in vacuo to a residue which was dissolved in water and freeze-dried to obtain 475 mg. of white powder. The antibiotic was identified by the mass spectrum of an N-acetyl-O-trimethylsilyl derivative which had characteristic ions at m/e 912 (M+-15), 722, 663, and 448. The nmr spectrum had δ 1.01 (CH₃, t), 1.78 (CH₂, m), and 2.44 (CH₂, t) for the butanoyl group along with signals expected for the other parts of the molecule.

The in vitro activity of this butyryl derivative was similar to that of AM31 β and it protected mice against lethal infections of *Klebsiella pneumonia* at 256 mg./kg. of body weight.

EXAMPLE 10

Preparation of the Octanoyl and Dodecanoyl Derivatives of AM31α

The octanoyl and dodecanoyl derivatives of AM31α were prepared by the procedure of Example 8 except that caprylic anhydride and lauric anhydride, respectively, were employed in place of the butyric anhydride of that examle. These derivatives possessed in vitro activity but significantly less (about 1/50) than that of AM31β.

EXAMPLE 11

Preparation of AM31β from the Daiminoalditol

The N,N'-diethoxycarbonyldiaminoalditol (VI) was prepared from the diaminoalditol (obtained from the antibiotic hydrolyzate) by a procedure essentially the same as that employed by Nishimura et al(1) to prepare N,N'-diethoxycarbonyl-2-deoxystreptamine. To a solution of 5.0 g. of (VI) in dry dimethylformamide was added 500 mg. of anhydrous p-toluenesulfonic

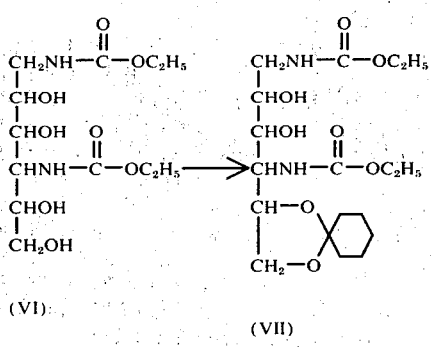

(VI)　　　　　　　　　(VII)

acid and 10 ml. of dry 1,1-dimethoxycyclohexane. The resulting solution was stirred at 50°C. in vacuo (33 Torr.) for two hours and then evaporated to a residue which was mixed vigorously with ethyl acetate and a saturated aqueous solution of barium hydroxide. The organic layer was separted, washed with water and evaporated to the crude mono-O-cyclohexylidene-N,N-diethoxycarbonyldiaminoalditol (VII), weight 5.2 g. A solution of (VII) (1.0 g.) in 20 ml. of dry benzene-dioxane (2:1) was mixed with 2.0 g. of Drierite, 2.0 g. of dried mercuric cyanide, and 2.0 g. of 3,4,6-tri-O-acetyl-N-p-methoxybenzylidene-α-D-glucosaminyl bromide (2) and the mixture was stirred at room temperature for 5 hours. The Drierite was removed by filtration and the filtrate was evaporated to an oil which was dissolved in chloroform, washed with aqueous NaHCO₃ and with water, and then evaporated to a viscous oil consisting of the desired condensation product (VII), other isomers, and impurities (1) Nishimura et al., Bull. Chem. Soc. Japan 43, 2960 (1970).
(2) Hardy et al., J. Chem. Soc., 3360 (1963).

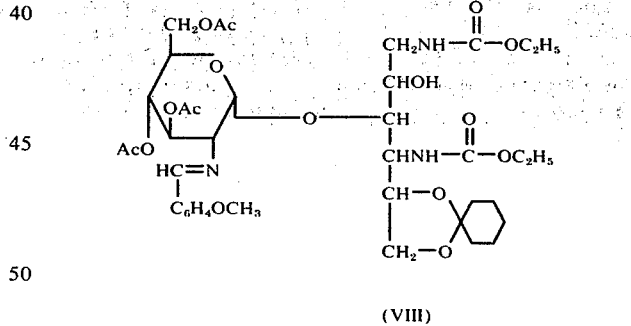

(VIII)

The viscous oil containing (VIII) was dissolved in 5 ml. of methanol and 2.5 ml. of 50% acetic acid was added. This solution was heated on a steam bath for one hour and evaporated to an oil which was dissolved in 100 ml. of methanol. This solution was cooled in an ice bath, 30 ml. of propionic anhydride was added, and the reaction mixture then allowed to stand at room temperature overnight. The reaction mixture was then evaporated to a syrup which was then stirred overnight at room temperature with 100 ml. of saturated aqueous barium hydroxide in a sealed flask. The excess barium hydroxide was removed by precipitation with CO₂. The filtrate contained the antibiotic AM31β which could be purified by ion exchange chromatography on Amberlite IRC-50 (NH₄+) or Dowex 50-X8 (NH₄+) as previously described for the natural antibiotic.

We claim:
1. A compound selected from the group consisting of those of the formula:

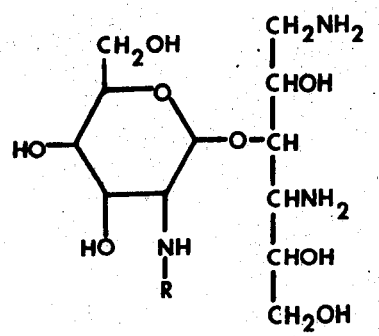

wherein R is selected from the group consisting of hydrogen, formyl, and alkanoyl having up to 12 carbon atoms; and the pharmaceutically acceptable acid-addition salts thereof.

2. A compound according to claim 1 wherein R is hydrogen.
3. A compound according to claim 1 wherein R is formyl.
4. A compound according to claim 1 wherein R is acetyl.
5. A compound according to claim 1 wherein R is propionyl.
6. A compound according to claim 1 wherein R is butyryl.
7. A compound according to claim 1 wherein R is octanoyl.
8. A compound acording to claim 1 wherein R is dodecanoyl.
9. The antibiotic free base according to claim 2.
10. The antibiotic free base according to claim 3.
11. The antibiotic free base according to claim 4.
12. The antibiotic free base according to claim 5.
13. The antibiotic free base according to claim 6.
14. The antibiotic free base according to claim 7.
15. The antibiotic free base according to claim 8.

* * * * *